(12) United States Patent
McMillan

(10) Patent No.: US 11,402,073 B1
(45) Date of Patent: Aug. 2, 2022

(54) UNIVERSAL RETROFIT AND COMPLIMENTARY LIGHT ASSEMBLY

(71) Applicant: George Erik McMillan, Hickory, NC (US)

(72) Inventor: George Erik McMillan, Hickory, NC (US)

(73) Assignee: EPIC Universal Technologies, LLC, Hickory, NC (US)

( * ) Notice: Subject to any disclaimer, the term of this patent is extended or adjusted under 35 U.S.C. 154(b) by 0 days.

(21) Appl. No.: 17/328,173

(22) Filed: May 24, 2021

Related U.S. Application Data

(60) Provisional application No. 63/029,108, filed on May 22, 2020.

(51) Int. Cl.
| | |
|---|---|
| *F21S 8/04* | (2006.01) |
| *F21V 21/088* | (2006.01) |
| *F21S 2/00* | (2016.01) |
| *F21V 23/00* | (2015.01) |
| *F21Y 109/00* | (2016.01) |
| *F21Y 115/10* | (2016.01) |

(52) U.S. Cl.
CPC ............. *F21S 8/04* (2013.01); *F21S 2/005* (2013.01); *F21V 21/088* (2013.01); *F21V 23/009* (2013.01); *F21Y 2109/00* (2016.08); *F21Y 2115/10* (2016.08)

(58) Field of Classification Search
CPC ......... F21S 8/04; F21S 9/022; F21Y 2115/10; F21Y 2113/10
See application file for complete search history.

(56) References Cited

U.S. PATENT DOCUMENTS

| | | | | |
|---|---|---|---|---|
| 9,069,106 | B1* | 6/2015 | Blessitt | G02B 6/0073 |
| 9,671,095 | B1* | 6/2017 | Sorensen | F21V 21/048 |
| 2014/0036503 | A1* | 2/2014 | Olsen | F21V 21/048 |
| | | | | 362/249.02 |

* cited by examiner

*Primary Examiner* — William J Carter
(74) *Attorney, Agent, or Firm* — Ascentage Patent Law, LLC; Travis Lee Johnson

(57) ABSTRACT

In one aspect, a retrofit and complimentary light assembly for emitting light can be installed in a ceiling with an existing light fixture as a secondary source to provide UVC emitting light for sterilization purposes or alternative visible light for aesthetic purposes. In yet another embodiment, it can be installed as a standalone light system without an existing light fixture into a ceiling with T-bar supports.

11 Claims, 9 Drawing Sheets

UNIVERSAL RETROFIT AND COMPLIMENTARY LIGHT ASSEMBLY

TECHNICAL FIELD

The present invention generally relates to ceiling light fixtures, and particularly to light fixtures that are configured to retrofit onto an existing light fixture.

BACKGROUND

In medical facilities, it is desirable, and sometimes even necessary, to eradicate germs, viruses, and microbes from the air and surfaces of rooms. One way to eradicate these biological threats is to expose a room to ultraviolet ("UV") light having a wavelength in a specific range for a period of time. For example, light having a wavelength between 200-280 nm, also known as UVC light, can kill airborne and surface biological threats. However, it is expensive to remove existing light fixtures that emit visible light to light a room in order to replace the existing fixture with a light fixture that emits UVC light. Also, it is not environmentally friendly to dispose of functional lights.

It is desirable to quickly, efficiently, and inexpensively provide an UVC light fixture in locations that already have existing light fixtures. Accordingly, it is desirable to have a UVC light fixture that attaches to an existing light fixture.

SUMMARY

UVC light can be used to clear a room of airborne and surface level biological threats, but it is costly and inefficient to replace existing light fixtures with light fixtures that emit UVC light. Accordingly, it is desirable to have a retrofit light fixture that is installed to work in conjunction with the existing light fixture.

According to some embodiments, a retrofit and complimentary light system, includes a frame having outer perimeter, an inner perimeter, a frontside and a backside, an aperture formed by the inner perimeter of the frame, which in some variants could include a translucent panel disposed over the aperture, at least one light emitting element disposed on the front side of the frame between the outer and inner perimeter, and two or more clips attached to the backside of the frame, wherein the frame and the two or more clips are configured to attach to a support system that supports an existing light fixture and to cover at least a portion of the existing light fixture.

In some variants of the embodiment the LED emitters are configured to emit light having a wavelength between 200-280 nm, which is considered in the UV spectrum known for killing viruses. Alternatively, the LED emitters could be any wavelength of light and be controllable or changeable to generate light with the visible spectrum so as to complement the existing light fixture. The intensity of the output of the LEDs can also be controllable.

In some variants, the frame has four perpendicular sides with each side including a clip that can slide onto a T-bar support in the ceiling. Further yet, two of the four clips are positioned in the same direction so as to be slide onto the T-bars in that direction, while the other two clips are positioned in the same direction that is orthogonal to the first two clips, to be slide onto the T-bars in that direction.

With the pairs clips forming a directional manner of sliding onto the T-bars, they are often installed in a diagonal manner.

Also contemplated herein is a method of installing a retrofit and complimentary light fixture, wherein the retrofit and complimentary light fixture includes a frame outer perimeter, an inner perimeter, a frontside and a backside, an aperture formed by the inner perimeter of the frame, LED emitters disposed on the front side of the frame between the outer and inner perimeter, and four clips attached to each of four sides of the frame on the backside, and wherein the four clips form two pairs, each pair position orthogonal to the other pair. The method comprises placing the retrofit and complimentary light fixture near an existing light fixture located in a ceiling having T-bars that support an existing light fixture and ceiling tiles. Then sliding the retrofit and complimentary light fixture onto the T-bars about the existing light fixture to engage each of the four clips to the corresponding T-bars so that the frame is primarily disposed over the frontside (viewable from below) of the T-bars. This enables the aperture to allow an optimum amount of light out from the existing light fixture. Then connecting the retrofit and complimentary light fixture to a power source.

Of course, the present invention is not limited to the above features and advantages. Those of ordinary skill in the art will recognize additional features and advantages upon reading the following detailed description, and upon viewing the accompanying drawings.

DETAILED DESCRIPTION

As noted above one of the purposes of the present embodiments is to provide a secondary lighting source about an existing light fixture without being disruptive to the existing light fixture. There are several reasons for wanting a secondary lighting source, which include sterilization if the secondary light source is configured with UV or UVC emitting LEDs that emit wavelengths between 200 and 280 nm or close thereto that are known to be effective when sterilizing the surrounding areas. This secondary light can thus be used when there are no occupants in the room and off-hours, such as when the existing lights are generally turned off.

In one example, this secondary light or retrofit and complimentary light assembly can be configured electrically such that it cannot be turned on if the existing or primary light fixture is on.

In alternative configurations and use cases, the retrofit and complimentary light assembly can include LEDs that emit a plurality of visible wavelengths that are controllable to create an enhancement to the existing light fixture, or otherwise transform the light in a room under one type of setting to another. For example, when used in a conference-style room the existing light fixtures might be used as the primary light source and illuminated to provide appropriate demonstration or working light. Later the conference-style can be transformed into an after-hours meet-and-greet where mood lighting is more appropriate. In certain hospital and other care facilities the ability to control the color of light can assist with helping calm occupants or patients in an otherwise stressful environment.

In each of these use cases described above, there is no need to remove or get rid of the existing light fixture, thus a system and method that can provide the above solutions while being able to easily integrate with the existing light fixture is desirable. For at least the above use cases and needs described the embodiments taught below are presented to accomplish those objectives and more.

Figure 1:
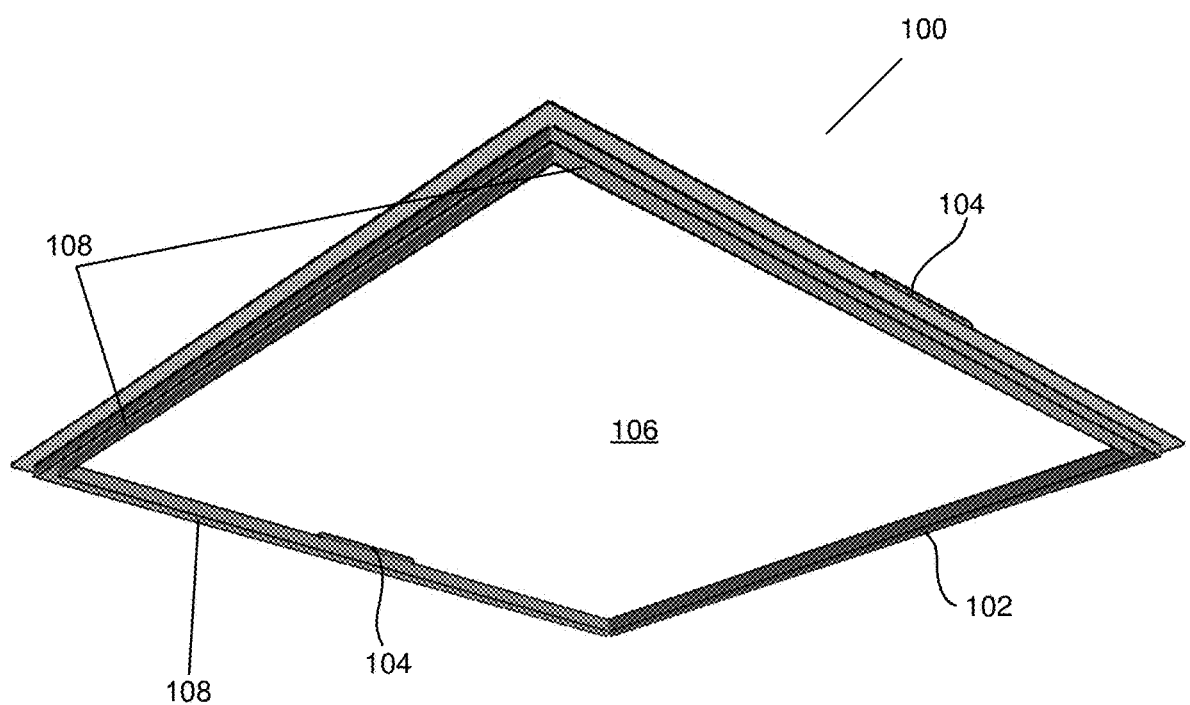
FIG. 1 is an illustration of a frontside perspective view of an exemplary retrofit and complimentary light assembly.
Figure 2:
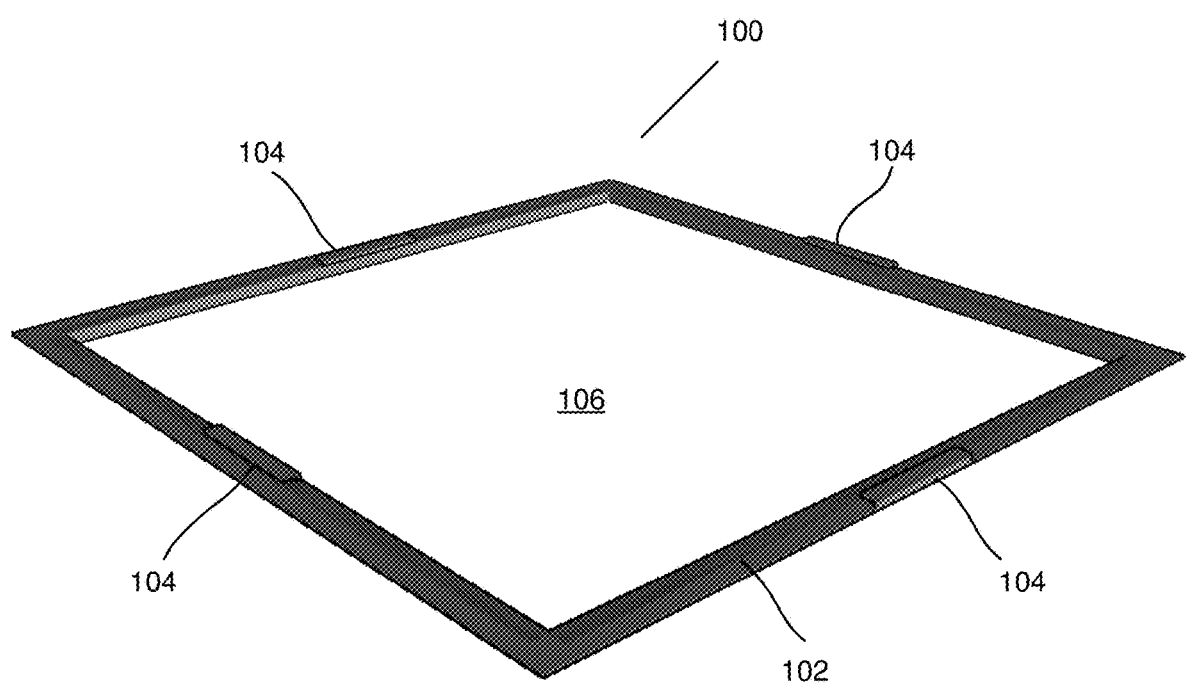
FIG. 2 illustrates a backside perspective view of the exemplary retrofit light assembly of FIG. 1.

FIGS. 1 and 2 are illustrations of a retrofit and complimentary light assembly 100, according to an example embodiment. The retrofit and complimentary light assembly includes a frame 102 having clips 104, an aperture 106, and light emitting diodes or LEDs 108. Although two or four clips 104 are shown, any suitable number of clips can be used. The aperture 106 can include a translucent panel so as to let light transmit through the aperture 106. As noted, the LED emitters can be configured to emit light having a wavelength between 200-280 nm, also known as UVC light. In FIG. 1 the LEDs 108 are shown on the frontside of the frame between an outer perimeter and an inner perimeter. The inner perimeter forming the aperture 106. In FIG. 2 the clips 104 are shown attached to the backside of the frame 102 and configured to attach to the T-bar of a ceiling. Once attached these clips will mostly be out of sight from below. The clips as shown are designed such that two clips form a pair to be slid onto the T-bars along a first direction and another two clips for a second pair that formed and configured to be slid onto the T-bar frame in a second direction that is orthogonal to the first direction.

FIGS. 3A-E the steps of installing the retrofit and complimentary light assembly 100 in a ceiling about an existing light fixture. In the exemplary embodiment shown the existing light fixture is a troffer light system, but the principles conveyed can be applied to varying styles of light fixtures, especially those used in a ceiling having a support structure such as one that uses T-bar supports.

Figure 3A:
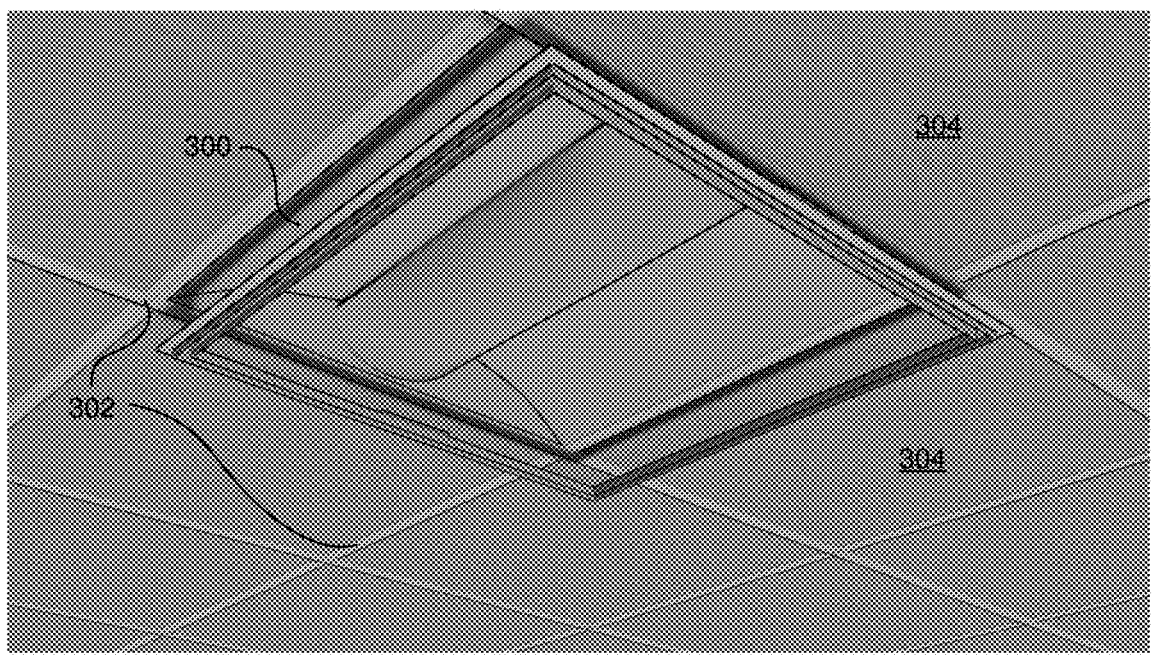
FIGS. 3A-E illustrate the steps of installing retrofit and complimentary light assembly in a ceiling about an existing light fixture.
Figure 3B:
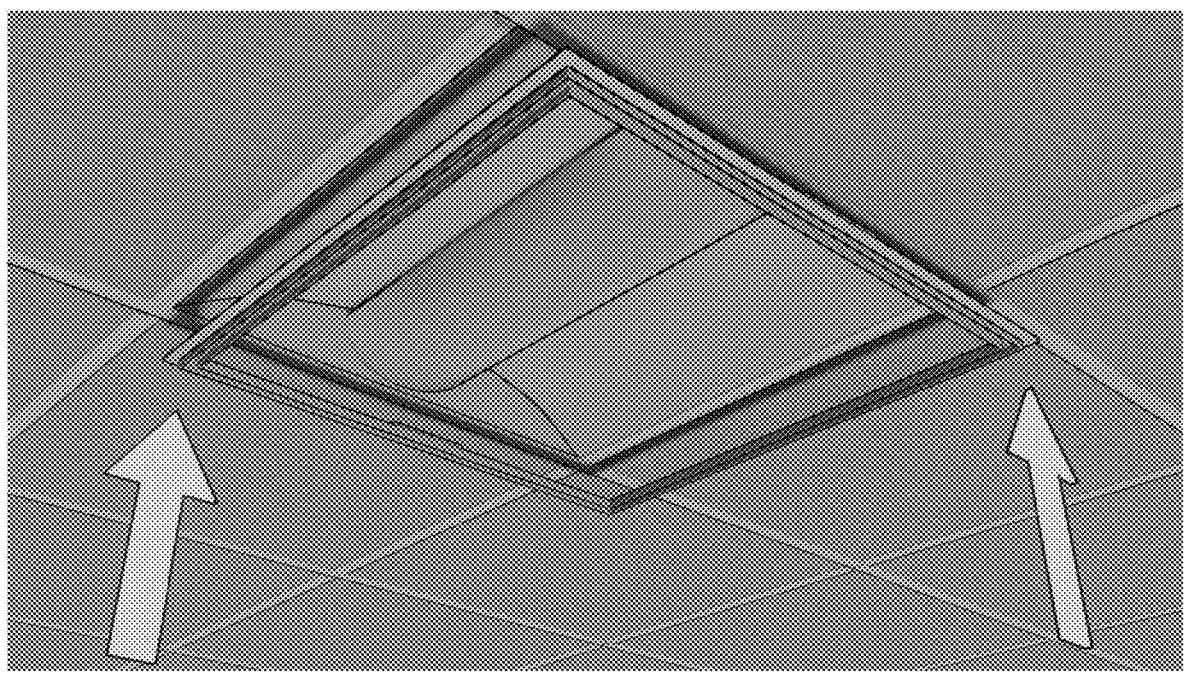
Figure 3C:
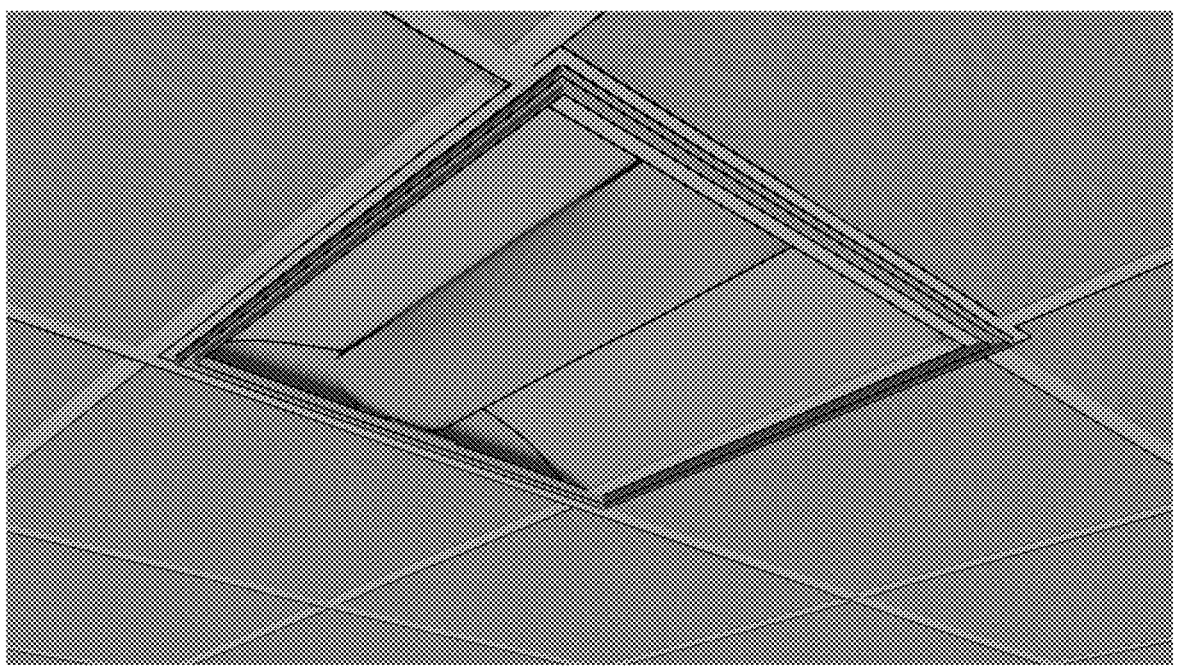

In many commercial buildings, a troffer light system 300 is installed in a ceiling and supported by T-bars 302. The retrofit and complimentary light assembly 100 can be configured to a size and geometry that is designed to fit over the existing troffer light system 300 and to mount to the existing T-bars 302 utilizing the clips 104. For example, this could be a 2×2 or 2×4 panel or light fixture. The ceiling as shown also has tiles 304 that are supported by the T-bars 302. To install the retrofit and complimentary light assembly 100, the installer places 100 near the existing light fixture, such as shown in FIG. 3A. Then the installer pushes or moves the light assembly 100 into ceiling where the clips are just offset from the T-bars as shown in FIG. 3B and completed in FIG. 3C.

Figure 3D:
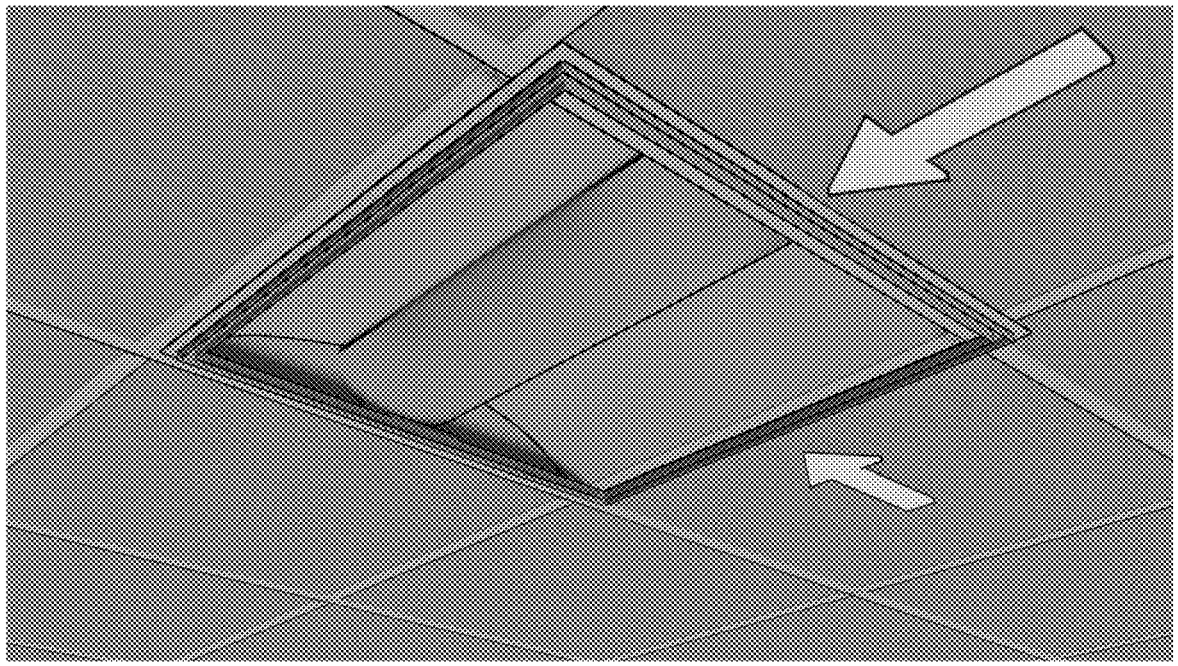
Figure 3E:
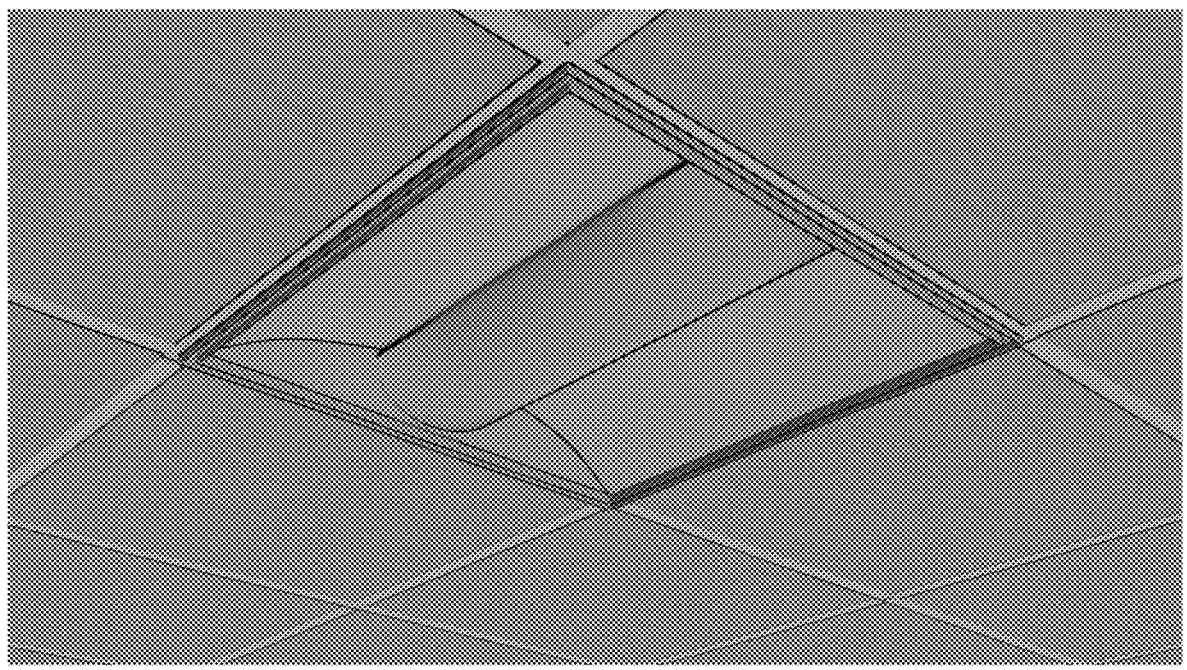

Once the light assembly 100 is flush with the ceiling the user slides the light assembly 100 in the direction of each pair of clips. This can be done at one direction at a time, for example sliding it in a first direction until slid into place with respect to the first pair of clips and then along a second direction until fit in position with respect to the second pair of clips. Alternatively, the user can slide the light assembly 100 at a roughly 45-degree angle (diagonally) so that all of the clips 104 slide between the T-bar 302 mount and the ceiling tile 304 at the same time. The direction of sliding with respect to each pair of clips is shown in FIG. 3D. Once positioned into place, as shown in FIG. 3E the clips 104 are positioned between the T-bar 304 and the existing fixture 300. In some variations the clips are disposed between the T-bar 304 and the ceiling tile. The final and desired position as shown in FIG. 3E is such that a majority of the frame 102 is disposed over the frontside of the T-bar supports, so as to align the aperture 106 to allow the optimal amount of light through from the existing light fixture. The term optimal is meant to allow as much light through without substantially interfering with the light emission of the existing light fixture. The frame does include a minimal amount of height, which can inhibit a very small amount of light, but that could also be negligent based on the style of existing light fixture installed. Thus, whether any light blockage occurs is dependent on the current light fixture. More importantly is the aperture is aligned and matches as closely to the existing opening of the light fixture. Thus, be having a majority of the frame disposed over the T-bar structure, minimal impediments result. A majority of the frame can include greater than 80%, greater than 90% and greater than 95% of the frame when installed is disposed over the T-bar structure.

It should be noted that the embodiments shown have one clip positioned centrally along each side. It is within the scope of this invention to have more than one clip on each side, or to even have one or more sides devoid of clips.

Figure 4:
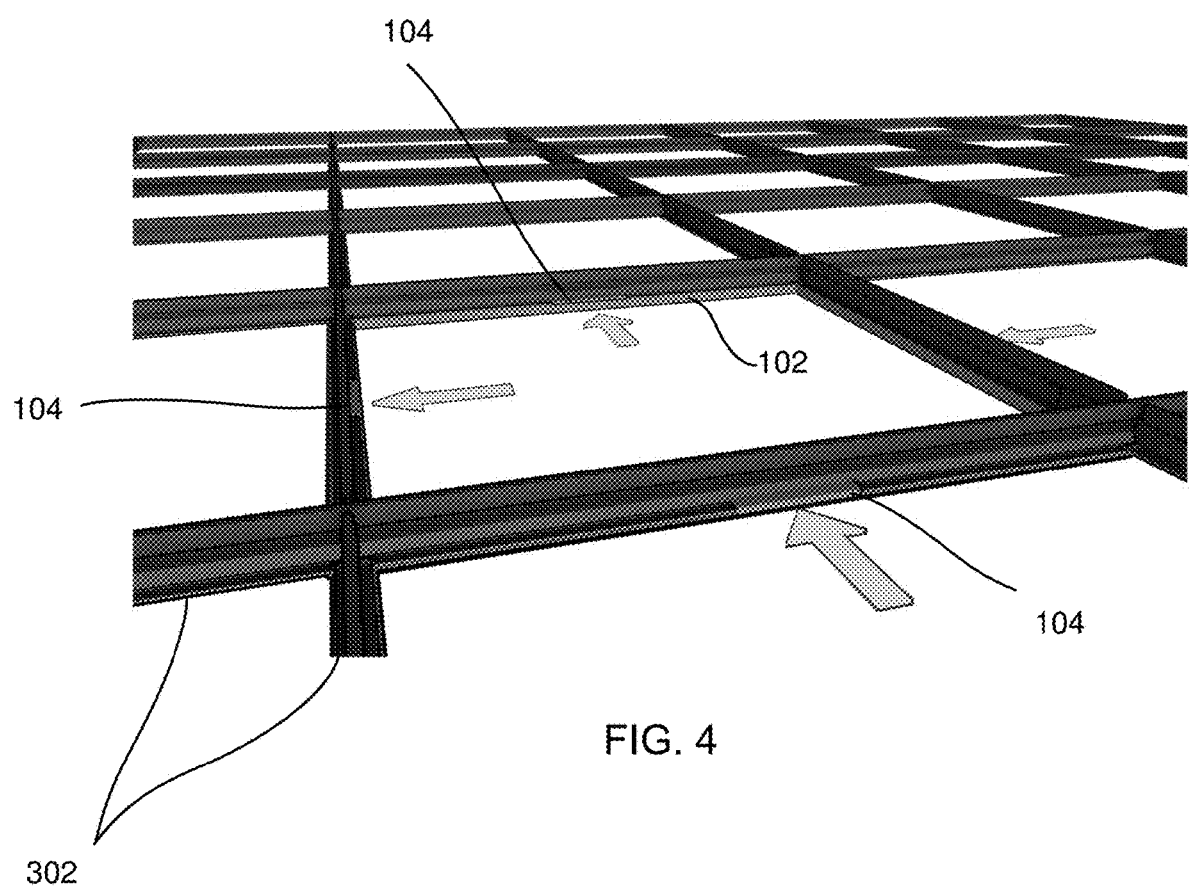
FIG. 4 illustrates the retrofit light assembly of FIGS. 1-2 installed on a T-Bar Frame.

FIG. 4 illustrates another view of the light assembly 100 installed in a T-Bar ceiling frame 302 without a troffer light or other ceiling tiles in place. The light assembly 100 can also be installed where only a ceiling tile exists; however, it would have to be tied into another power source, as shown in FIG. 6B.

Figure 5:
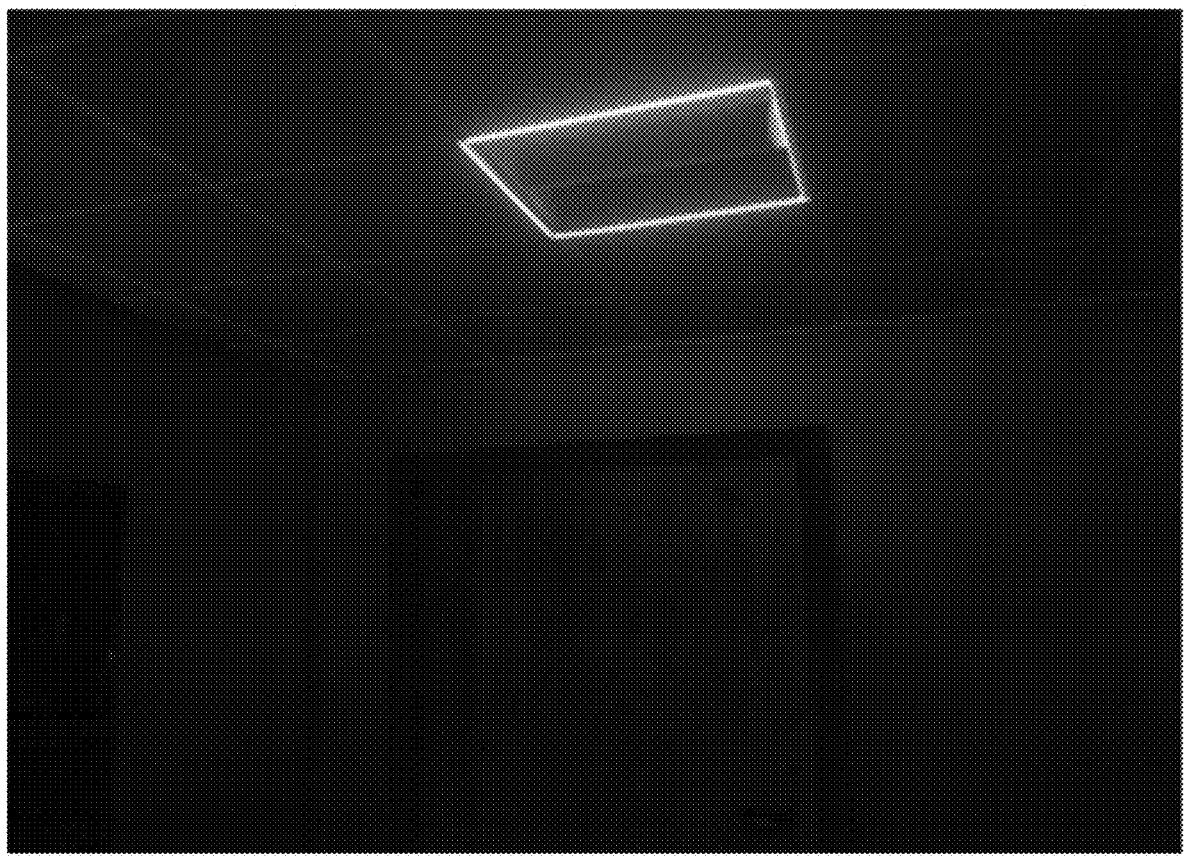
FIG. 5 illustrates another embodiment of a retrofit light assembly in active mode.

FIG. 5 illustrates an embodiment of the light assembly 100 installed and illuminating separate from the light fixture. In this embodiment, the LED emitters are located in the frame. The LED emitters includes at least LED emitter that emits UVC light. Optionally, the LED emitters may include LED emitters that emit visible light of different colors as previously noted. For example, when the retrofit light assembly is operated to emit UVC light, an LED is operated that emits colored light, such as purple or blue, to indicate to an observer that the UVC light is being emitted.

Figure 6A:
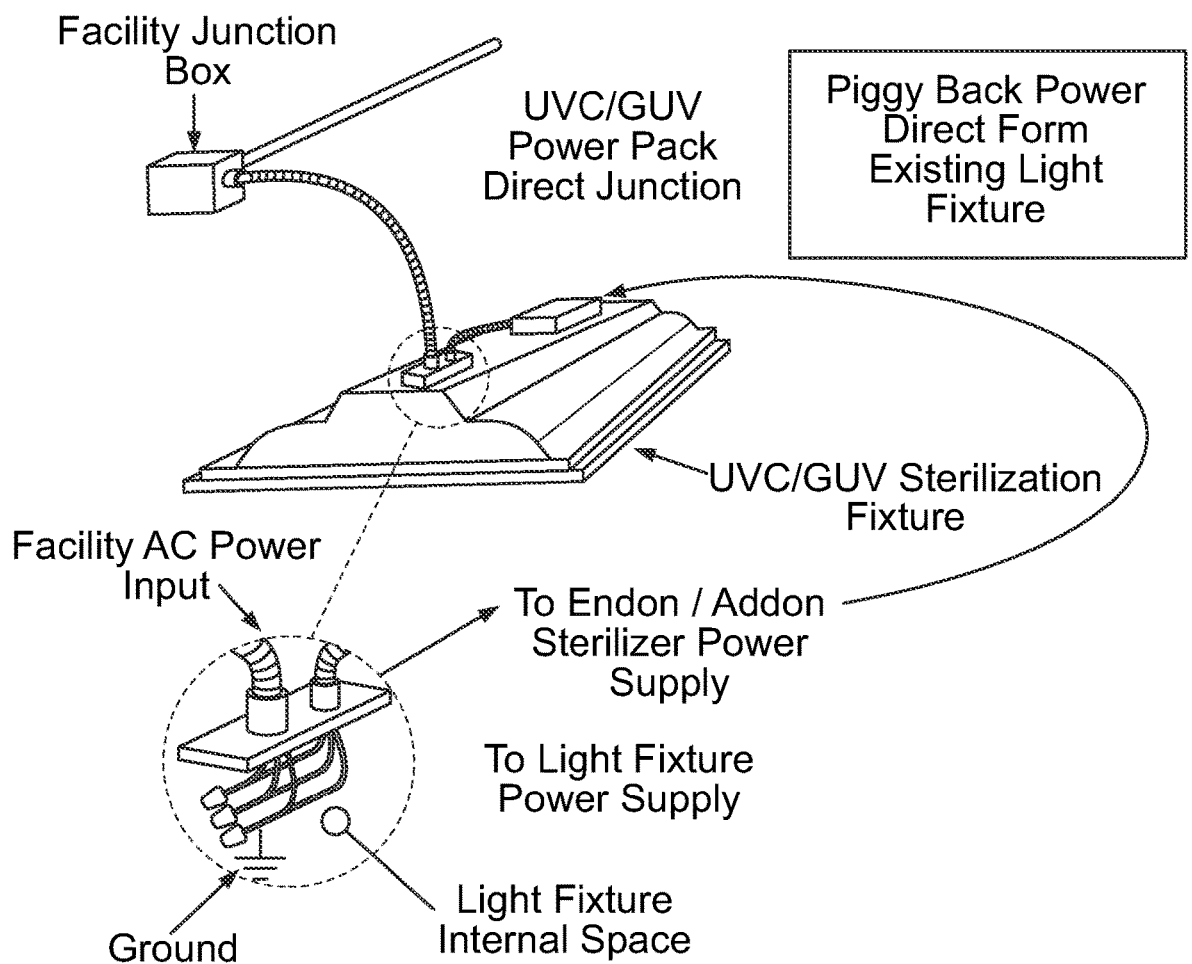
FIGS. 6A-B illustrate wiring to provide power to the retrofit light assembly.
Figure 6B:
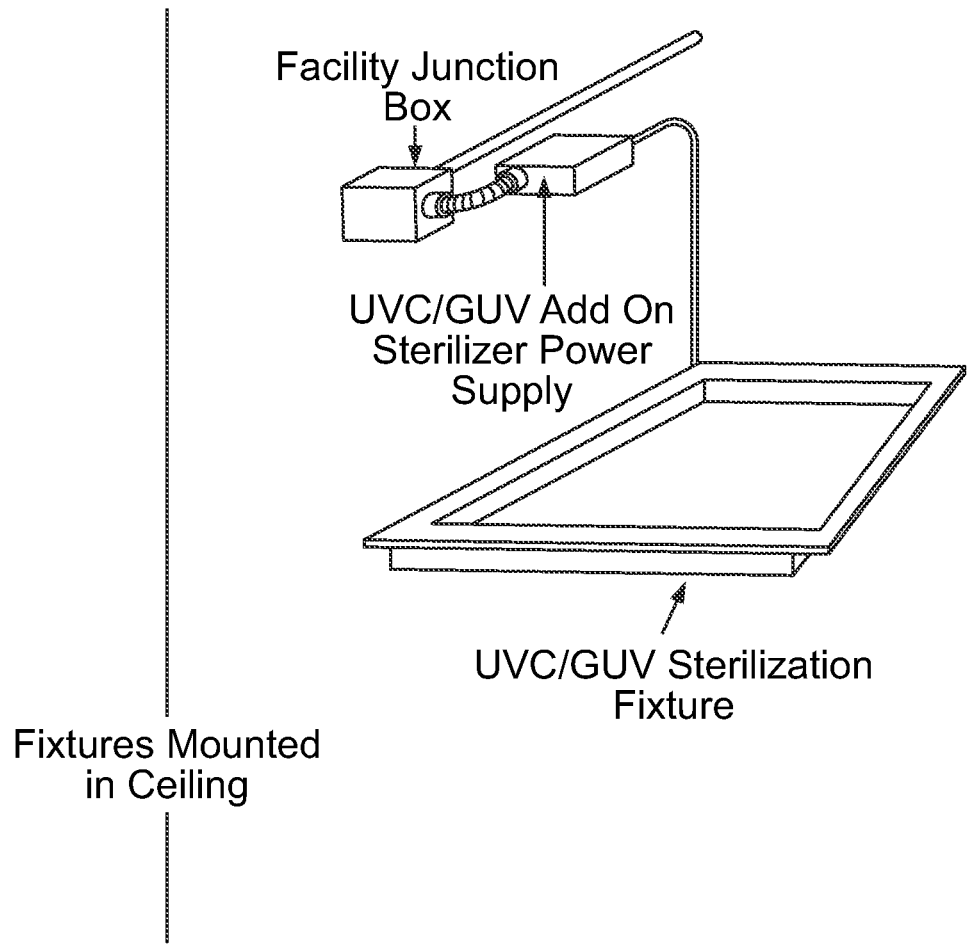

FIG. 6A illustrates one way to provide power to the retrofit light assembly by wiring the retrofit light assembly to power supply for the existing light assembly. In this embodiment, power line from the assembly is wired to the existing light fixture to provide power to the light fixture. A connection is spliced from the input from the power line and is wired to ground and to a power pack for the retrofit light assembly. The power pack may be installed on top of the existing light assembly or installed within the ceiling at a location convenient to the installer. The power pack is electrically connected to the light panel of the retrofit light assembly.

FIG. 8B illustrates another way to provide power to the retrofit light assembly. In this embodiment, the retrofit light assembly is directly hard wired to a facility junction box. A power pack is wired directly to the facility junction box, and power pack is electrically connected to the retrofit light panel. The power pack may include an alternating current to direct current (AC-DC) converter, a driver within the housing that is configured to provide DC from the AC-DC converter to the LED light fixtures, and other wiring, circuitry or elements needed to provide power to the retrofit light assembly. This embodiment is suitable for whether the retrofit light assembly is installed over a ceiling tile or over an existing light fixture.

Once the retrofit light assembly is wired to power, it is necessary to provide control of the light assembly. This can be done by any suitable method such as installing a hardwire controller (such as switches or dimmers) or by using a wireless controller.

Of course, the present invention is not limited to the above features and advantages. Those of ordinary skill in the art will recognize additional features and advantages upon reading the following detailed description, and upon viewing the accompanying drawings.

Notably, modifications and other embodiments of the disclosed invention(s) will come to mind to one skilled in the art having the benefit of the teachings presented in the foregoing descriptions and the associated drawings. Therefore, it is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

What is claimed:

1. A new construction or retrofit and complimentary light system, comprising: a frame having an outer perimeter, an inner perimeter, a frontside and a backside; an aperture formed by the inner perimeter of the frame; one or more LED emitters disposed on the front side of the frame between the outer and inner perimeter; and
   two or more clips attached to the backside of the frame, wherein the frame and the two or more clips are configured to attach to a support system that supports an existing light fixture and to cover at least a portion of the support system, and
   wherein the aperture of the frame, when installed below the existing light fixture, allows an optimum amount of visible light from the existing light fixture to pass through the aperture; wherein the one or more of the LED emitters are configured to emit light having a wavelength between 200-280 nm.

2. The new construction or retrofit and complimentary light system of claim 1, wherein the aperture includes a translucent panel so as to let light from the existing light fixture transmit through the light emitting panel.

3. The new construction or retrofit and complimentary light system of claim 2, wherein the translucent panel covers an entirety of the existing light fixture.

4. The new construction or retrofit and complimentary light system of claim 1, wherein the support system comprises T-bars and the two or more clips attach to the T-bars on the backside that is not viewable from below.

5. The new construction or retrofit and complimentary light system of claim 4, wherein the frame includes four sides, and the two or more clips include two pairs of complementary clips.

6. The new construction or retrofit and complimentary light system of claim 5, wherein a first pair of the two pairs are disposed on sides that are parallel to each other, and the each clip of the first pair of clips are disposed in the same direction.

7. The new construction or retrofit and complimentary light system of claim 6, wherein the remaining second pair of the two pairs are disposed on two sides that are each perpendicular to the parallel sides, and each clip of the second pair are disposed in the same direction, said direction being orthogonal to the direction of the clips of the first pair.

8. The new construction or retrofit and complimentary light system of claim 7, wherein the aperture is sized so as to not interfere or substantially interfere with light emitting from the existing light fixture.

9. The new construction or retrofit and complimentary light system of claim 1, further including electrical connectors configured to attach to the existing light fixture.

10. The new construction or retrofit and complimentary light system of claim 1, further including electrical connectors and driver configured to attach to a power source.

11. A method of installing a new construction or retrofit and complimentary light fixture, wherein the retrofit and complimentary light fixture includes a frame outer perimeter, an inner perimeter, a frontside and a backside, an aperture formed by the inner perimeter of the frame, LED emitters having a wavelength between 200-280 nm disposed on the front side of the frame between the outer and inner perimeter, and four clips attached to each of four sides of the frame on the backside, and wherein the four clips form two pairs, each pair position orthogonal to the other pair, the method comprising:
   placing the retrofit and complimentary light fixture near an existing light fixture located in a ceiling having T-bars that support an existing light fixture and ceiling tiles;
   sliding the retrofit and complimentary light fixture onto the T-bars about the existing light fixture to engage each of the four clips to the corresponding T-bars, and wherein the frame is primarily disposed over the frontside of the T-bars such that the aperture allows an optimum amount of visible light out from the existing light fixture, the frontside is viewable from below; and
   connecting the retrofit and complimentary light fixture to a power source.

\* \* \* \* \*